United States Patent [19]

Duncan

[11] 3,952,745
[45] Apr. 27, 1976

[54] DISPOSABLE DIAPER HAVING READILY FLUSHABLE ABSORBENT MEDIA AND IMPROVED PAD INTERGRITY IN USE

[75] Inventor: Robert C. Duncan, Wyoming, Ohio
[73] Assignee: The Procter & Gamble Company, Cincinnati, Ohio
[22] Filed: Nov. 19, 1974
[21] Appl. No.: 525,254

[52] U.S. Cl.............................. 128/287; 128/284
[51] Int. Cl.² ........................................ A61F 13/16
[58] Field of Search................ 128/284, 287, 290 R

[56] References Cited
UNITED STATES PATENTS

| | | | |
|---|---|---|---|
| 3,586,000 | 6/1971 | Ness.................................... | 128/287 |
| 3,636,952 | 1/1972 | George .............................. | 128/287 |
| 3,865,111 | 2/1975 | Brooks................................ | 128/287 |
| 3,868,287 | 2/1975 | Lewyckyj........................... | 128/284 X |
| R26,151 | 1/1967 | Duncan et al. .................... | 128/284 |

*Primary Examiner*—Aldrich F. Medbery
*Attorney, Agent, or Firm*—E. Kelly Linman; Frederick H. Braun; John V. Gorman

[57] ABSTRACT

A disposable diaper is provided with an absorbent pad comprised of airfelt or a similar low-strength absorbent material enclosed by an envelope of wet strength tissue. The absorbent pad is preferably enclosed between a liquid-retaining backsheet and a liquid-pervious topsheet secured in superposed relation to the liquid-retaining backsheet. Because the wet strength tissue envelope surrounding the absorbent core material tends to cling to the wetted pad after removal of the liquid-retaining backsheet, it tends to prevent hydraulic erosion of the absorbent media and therefore interferes with pad flushability. If a non-wet strength tissue is utilized on one or both sides of the absorbent media it will readily dissociate upon immersion in water and thereby promote pad flushability. However, such an absorbent pad lacks integrity in use due to the low strength of the absorbent media employed. In accordance with the present invention, wet strength tissue is utilized on both surfaces of the absorbent pad to provide support for the low strength absorbent media and, accordingly, improved in use pad integrity without adversely affecting pad flushability. This is preferably accomplished by adhering the layer of wet strength tissue adjacent the liquid-retaining backsheet directly to the backsheet so that when the liquid-retaining backsheet is stripped from the diaper prior to flushing, a broad central panel of the wet strength tissue envelope is removed from the absorbent pad to expose the absorbent media contained therein to hydraulic erosion during the rinsing operation.

8 Claims, 3 Drawing Figures

DISPOSABLE DIAPER HAVING READILY FLUSHABLE ABSORBENT MEDIA AND IMPROVED PAD INTERGRITY IN USE

BACKGROUND OF THE INVENTION

The present invention relates generally to disposable diapers and, more particularly, to a new and improved disposable absorbent diaper pad construction which provides improved pad integrity in use without adversely affecting pad flushability.

In recent years, improvements in disposable diapers have revolutionized the diapering of infants. As the term "disposable" implies, these diapers are designed to be discarded after a single use. Disposable diapers generally consist of an absorbent pad, a pad-covering topsheet which contacts the infant, and a liquid-impervious backsheet for containing liquid wastes within the absorbent pad. U.S. Pat. No. Re. 26,151 which issued to Duncan et al. on Jan. 31, 1967 is representative of such disposable diaper structures. As is taught by the Duncan et al. patent, a soiled diaper is preferably disposed of by stripping the moisture-impervious backsheet from the soiled absorbent portions of the structure prior to rinsing the soiled absorbent portions of the structure in a conventional toilet wherein it tends to disintegrate prior to flushing. When plies of creped cellulose wadding are employed as the absorbent media there is little or no need for enclosing the absorbent media within an envelope of wet strength tissue since the creped cellulose wadding generally has sufficient strength to provide satisfactory in use pad integrity. When, however, the absorbent media is comprised of a low-strength material such as air-laid wood pulp fluff, commonly referred to as airfelt, a strength-imparting envelope is generally necessary not only to provide satisfactory in use pad integrity, but also to avoid the dusting and linting problems commonly associated with such low-strength absorbent materials both during manufacture and in use. Failure to provide sufficient in use pad integrity in a disposable diaper adversely affects both its absorbency and its containment characteristics. Therefore a number of prior art disposable diaper structures have encapsulated the low strength absorbent media in an envelope of sheet material having at least some degree of wet strength, wet strength tissue paper being most commonly utilized. The chief disadvantage associated with such prior art structures, however, is that they do not disintegrate readily upon immersion in water unless the various layers of the structure are painstakingly disassembled by the user. Hence they are not readily flushable. The term "flushable" as used herein, is primarily intended to describe the ability of the absorbent media of a diaper pad structure to physically dissociate and structurally break down into small clumps of loose fibers by the normal action of rinsing the absorbent pad in water in an ordinary toilet bowl, without need for manually separating the various tissue layers employed in the absorbent pad of the diaper. All portions of the absorbent media should be capable of safely and harmlessly passing through a normal household sewage system without danger of clogging the system. Once the absorbent media has become dissociated from the portions of the diaper having at least some degree of wet strength, i.e., the topsheet and those portions of the tissue envelope which are immersed in the toilet bowl, the wet strength materials may either be flushed or wrapped within the moisture-impervious backsheet after rinsing for disposal in conventional solid waste disposal systems.

U.S. Pat. No. 3,636,952 which issued to George on Jan. 25, 1972 discloses a disposable diaper structure having an absorbent core comprised of airfelt contained within an envelope of cellulosic tissue, the various layers of the structure being secured together by means of embossing and gluing at their peripheries. The patent to George teaches that the diaper is preferably disposed of by stripping off and disposing of the moisture-impervious protective cover and then flushing the remainder of the structure in an ordinary toilet. However, as should be readily apparent from an inspection of the patent, the absorbent core material remains trapped between an envelope of cellulosic tissue paper after deposition in the toilet bowl and therefore the flushability of the structure is impaired unless the various layers of the structure are manually separated.

U.S. Pat. No. 3,586,000 which issued to Ness on June 22, 1971 likewise discloses a disposable diaper structure having a fluffed wood pulp absorbent filler encased on both sides by wet strength tissue. As with the patent to George, however, the absorbent media remains enclosed within an envelope of wet strength tissue upon stripping of the moisture-impervious backsheet prior to flushing.

OBJECTS OF THE INVENTION

In view of the disadvantages and shortcomings of prior art disposable diaper constructions, it is an object of the present invention to provide a disposable, single use diaper having improved in use pad integrity and in which the surface of the low-strength absorbent media is exposed directly to hydraulic erosion upon rinsing of the soiled portions of the diaper in a conventional toilet without need for manually disassembling a plurality of layers of tissue prior to depositing the structure therein.

It is a further object of the present invention to provide a disposable absorbent diaper having an absorbent pad comprised of a low-strength absorbent media such as airfelt enclosed within an envelope of wet strength tissue paper wherein a portion of the wet strength tissue paper envelope is either ruptured or completely removed from the absorbent pad upon stripping of the moisture-impervious backsheet from the remainder of the structure.

It is still a further object of the present invention to provide a disposable absorbent diaper pad wherein the surface of the absorbent media is exposed directly to hydraulic erosion during the rinsing operation, whereby said absorbent media may rapidly dissociate and disintegrate to more readily permit flushing of the pad in a conventional toilet bowl.

BRIEF DESCRIPTION OF THE DRAWINGS

While the specification concludes with claims particularly pointing out and distinctly claiming the present invention, it is believed that the invention will be better understood by reference to the following explanation and accompanying drawings in which:

DESCRIPTION OF THE PREFERRED EMBODIMENTS

Figure 1:
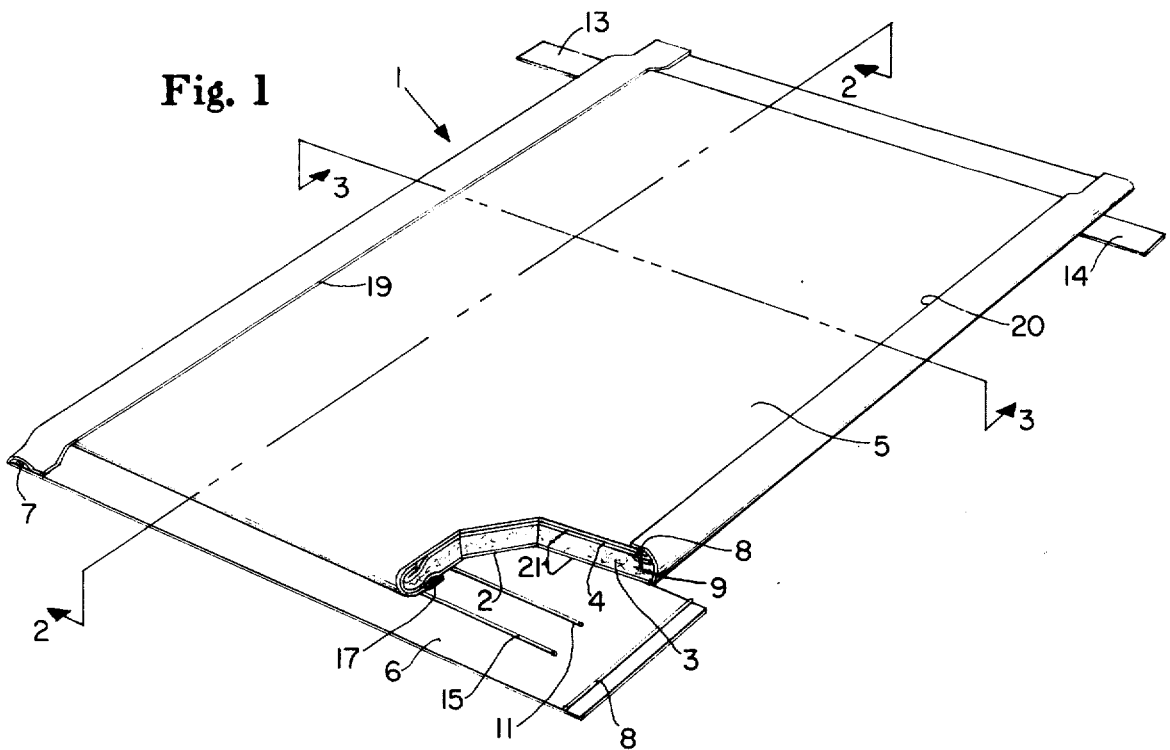
FIG. 1 is a perspective view of a preferred embodiment of a disposable diaper of the present invention with one corner section broken out to illustrate the relationship of the various structural elements.

FIG. 1 is illustrative of a preferred embodiment of a disposable diaper of the present invention. Typically, a disposable diaper 1 of the present invention comprises a liquid-impervious backsheet 6, a liquid absorbent pad 21, and a body contacting topsheet 5. The backsheet 6 may be made of plastic, treated paper, or the like and will typically wrap over the absorbent pad and topsheet at the edges to provide side flaps 19 and 20 which serve to improve the containment characteristics of the diaper, as taught by U.S. Pat. No. Re. 26,151 which issued to Duncan et al. on Jan. 31, 1967, said patent being hereby incorporated herein by reference. In a preferred embodiment of the present invention, the liquid absorbent pad 21 is constructed of comminuted wood pulp 3, generally referred to as airfelt, and is enveloped between a pair of tissue sheets 2 and 4 having at least moderate wet strength. The wet strength tissue sheets 2 and 4 are utilized to provide in use pad integrity and to prevent dusting or linting of the airfelt 3 through the porous, body contacting topsheet 5. The wet strength tissue envelope is generally desirable since the airfelt 3 has little or no inherent tensile strength. The body-contacting topsheet 5 is of a liquid-pervious, and preferably hydrophobic material. In the absence of a tissue envelope, the absorbent airfelt 3 tends to dust directly through the porous topsheet, thereby depositing lint on the wearer's skin and, in addition, creating a dusty environment.

Figure 2:
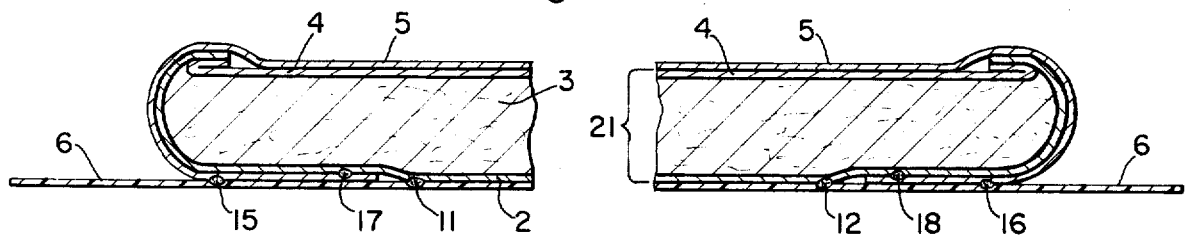
FIG. 2 is an enlarged sectional view of the disposable diaper illustrated in FIG. 1 taken along section line 2—2 of FIG. 1.
Figure 3:
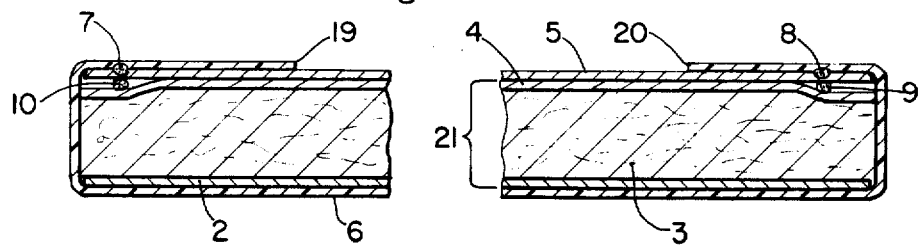
FIG. 3 is an enlarged sectional view of the disposable diaper illustrated in FIG. 1 taken along section line 3—3 of FIG. 1.

The manner in which the various elements are assembled is more clearly illustrated in FIGS. 2 and 3. As can be seen in FIG. 2, the topsheet 5 is folded about the absorbent pad 21 at the ends or waistband portions of the diaper. The overlapping portions of the topsheet 5 are secured directly to the backsheet 6 by means of beads of adhesive 15 and 16 extending essentially across the entire width of the absorbent pad 21. The absorbent media 3 which is preferably comprised of airfelt is contained between layers of wet strength tissue paper 2 and 4. The end portions of the uppermost layer of wet strength tissue paper 4 are folded back upon themselves, while the end portions of the lowermost layer of wet strength tissue paper 2 are folded back over the end portions of the uppermost layer of wet strength tissue paper to form an envelope about the absorbent media 3. The absorbent pad 21 is thus constrained within an outer envelope formed by the topsheet 5 and the moisture-impervious backsheet 6. The absorbent pad 21 is preferably secured to the overlapping portions of the topsheet 5 by means of beads of adhesive 17 and 18 which extend essentially across the entire width of the absorbent pad. Beads of adhesive 11 and 12 which also extend essentially across the entire width of the absorbent pad are preferably utilized to secure the lowermost layer of wet strength tissue paper 2 directly to the innermost surface of the moisture-impervious backsheet 6.

Referring now to FIG. 3, it can be seen that the liquid absorbent pad 21 is constrained along the edge portions of the diaper within the envelope formed by the liquid-pervious topsheet 5 and the overlapping edge portions of the moisture-impervious backsheet 6 which are joined together along the edge portions of the diaper by means of beads of adhesive 7 and 8 which preferably extend the entire length of the backsheet. It should be noted that the inner overlapping edge portions 19 and 20 of the moisture-impervious backsheet 6 are not secured directly to the topsheet in order to provide a gasketing action and hence better containment of exuded body fluids in accordance with the teachings of the aforementioned patent to Duncan et al. The uppermost surface of wet strength tissue layer 4 is preferably secured to the lowermost surface of the liquid-pervious topsheet 5 by means of beads of adhesive 9 and 10 which extend the entire length of the absorbent pad 21. Due to the liquid-pervious nature of the topsheet 5, beads of adhesive 9 and 10 are normally provided simply by migration of a portion of the adhesive utilized to form beads 7 and 8 directly through the liquid-pervious topsheet while the adhesive is in a liquid state.

A disposable diaper of the present invention is preferably secured in place about the waist of the wearer by means of pressure-sensitive adhesive tape fasteners 13 and 14 which are well known in the disposable diapers art.

When a disposable diaper 1 of the present invention has become soiled, the moisture-impervious backsheet 6 may be stripped from the remainder of the diaper to permit disposal of the soiled portions of the diaper by flushing in a conventional toilet. This is preferably accomplished by severing beads of adhesive 15 and 16 between the backsheet and the topsheet along the end portions of the diaper. Beads of adhesive 11 and 12 which secure the lowermost layer of wet strength tissue 2 directly to the moisture-impervious backsheet 6 are not severed, however, by the aforementioned stripping action. Beads of adhesive 11 and 12 must be sufficiently strong to securely bond the wet strength tissue layer 2 to the backsheet so that the stripping action applied to the backsheet will cause the lowermost panel of wet strength tissue to rupture outside the beads of adhesive and thereby cause that portion of the lowermost layer of wet strength tissue paper located intermediate the adhesive glue beads 11 and 12 to remain in adherent contact with the moisture-impervious backsheet 6 when the backsheet is removed from the remainder of the structure. Thus a large panel of wet strength tissue envelope utilized to impart strength to the low-strength liquid-absorbent media 3 in use is removed to permit rapid hydraulic erosion of the absorbent media remaining within the envelope upon rinsing of the soiled portions of the diaper in a toilet bowl.

Depending upon such factors as the degree of wet strength inherent in the tissue layers 2 and 4 and the liquid-pervious topsheet 5, the physical dimensions of the wet strength materials and the quantity of absorbent media 3 employed in the absorbent pad 21, it may be feasible to flush the wet strength materials in a conventional toilet bowl along with the absorbent media 3 which is readily dissociated by hydraulic erosion. To minimize the danger of clogging marginal plumbing systems, however, the wet strength materials may be removed from the toilet bowl as an integral unit after hydraulic erosion of the absorbent media 3 and rinsing of any fecal soil therefrom. The wet strength materials may then be wrapped in the moisture-impervious backsheet 6 for disposal in conventional solid waste disposal systems.

Thus, applicant's invention permits a combination of previously incompatible features into a single disposable diaper structure, i.e., the utilization of wet strength tissue paper on both sides of a low-strength absorbent media to provide greatly improved in use pad integrity without adversely affecting the flushability of the absorbent pad portion of the disposable diaper.

As will be apparent to those skilled in the art, adherence of the lowermost layer of wet strength tissue directly to the moisture-impervious backsheet could be accomplished by a variety of means including, for example, adhering the tissue layer to the backsheet throughout the entire area of their interface.

In yet another preferred embodiment of the present invention, a single bead of adhesive, i.e., adhesive bead 11, is utilized to secure the lowermost layer of wet strength tissue 2 directly to the moisture-impervious backsheet 6. Although a single bead of adhesive will not completely remove an entire panel of wet strength tissue from the absorbent pad 21, the single bead of adhesive 11 will cause the wet strength tissue envelope surrounding the absorbent media 3 to rupture when the moisture-impervious backsheet is stripped from the remainder of the structure, thereby exposing the absorbent media 3 to hydraulic erosion upon immersion of the soiled portions of the diaper in a toilet bowl. In such an embodiment, the moisture-impervious backsheet 6 is preferably stripped from the remainder of the diaper only along three sides, i.e., along adhesive beads 7, 8 and 15 thereby rupturing wet strength tissue layer 2 adjacent adhesive bead 11, and the soiled absorbent portions of the diaper are immersed in the toilet bowl and rinsed to remove any fecal soil as well as the absorbent media 3, while the moisture-impervious backsheet is retained in one hand. The moisture-impervious backsheet 6 remains secured to the topsheet 5 by means of adhesive bead 16 extending along an end or waistband portion of the diaper and to the lowermost layer of wet strength tissue 2 by means of adhesive bead 11 extending across the width of the absorbent pad 21, while the other portions of the wet strength tissue envelope remain secured to the topsheet by means of adhesive beads 9 and 10 extending along the edges of the diaper and adhesive beads 17 and 18 extending along the end or waistband portions of the diaper. Those portions of the diaper structure which do not readily disintegrate upon immersion in water, i.e., wet strength tissue layers 2 and 4 and the liquid-impervious topsheet 5, can, after rinsing of any fecal soil and removal of the absorbent media 3 by means of hydraulic erosion, be removed from the toilet bowl and wrapped within the moisture-impervious backsheet 6 for disposal in conventional solid waste disposal systems. Because the wet strength tissue layers 2 and 4 and the liquid-pervious topsheet 5 are disposed of in conventional solid waste disposal systems rather than by flushing in such an embodiment of the present invention, materials having much higher wet strengths may be employed in these areas, thus greatly improving the diaper's overall resistance to in use tearing and shredding without adversely affecting the flushability of the liquid absorbent media 3.

In still another embodiment of the present invention, the lowermost layer of wet strength tissue 2 may be adhered directly to the moisture-impervious backsheet 6 at a multiplicity of isolated locations so that the wet strength tissue envelope surrounding the absorbent media 3 becomes perforated as the moisture-impervious backsheet 6 is either partially or completely stripped from the remainder of the structure. The absorbent media 3 is thereby directly exposed to hydraulic erosion through the perforations in the wet strength tissue envelope upon immersion of the absorbent pad 21 in water.

In disposable diaper structures employing multiple plies of wet strength tissue to provide greatly improved pad integrity in use, the present invention may be practiced with equal facility simply by employing an adhesive which is sufficiently liquid during application to permeate all of the layers of wet strength tissue located intermediate the absorbent media 3 and the moisture-impervious backsheet 6 and which has sufficient strength to adhere the layers to each other and to the moisture-impervious backsheet so as to cause failure in the wet strength tissue plies rather than in the glue bond when the backsheet is stripped from the remainder of the diaper structure.

In a most preferred embodiment of the present invention, tissue layers 2 and 4 are comprised of wet strength tissue paper having a basis weight of about 12 pounds per 3,000 square ft., a dry tensile strength of between about 650 and about 950 grams per inch in the machine direction and between about 250 and about 400 grams per inch in the cross-machine direction, and a minimum wet tensile strength of at least about 55 grams per inch in the cross-machine direction. The dry stretch characteristics of the wet strength tissue layers 2 and 4 are preferably about 1 percent elongation under a tensile load of 90 grams per inch and about 2.2 percent elongation under a tensile load of 200 grams per inch, as measured in the machine direction. The wet strength tissue layers 2 and 4 are preferably assembled in the diaper with their machine direction aligned parallel to the direction of adhesive beads 11 and 12, i.e., parallel to the waistband portions of the diaper, to impart maximum strength to the waistband areas which are subject to the greatest tensile loads in use.

The backsheet 6 is preferably comprised of an embossed polyethylene film having a melt index between about 1.5 and about 5.4, a density between about 0.917 and about 0.926 grams per cubic centimeter, an unembossed caliper of about 1 mil, as measured under a load of approximately 95 grams per square inch, and an embossed caliper between about 3 and about 3½ mils, as measured under a load of approximately 95 grams per square inch. The embossed polyethylene film preferably has a machine direction tensile strength, as measured at 25 percent elongation, of at least about 800 grams per inch. One material which has been found particularly suitable in the present application is embossed polyethylene film No. 8020 which is available from the Monsanto Company of St. Louis, Mo.

Any number of commercially available topsheet materials may be employed in a disposable diaper of the present invention. The wet tensile strength of the topsheet material is preferably at least about 1000 grams per inch as measured in the machine direction and at least about 180 grams per inch as measured in the cross-machine direction. One material found particularly suitable and which is available from The Kendall Company, of Walpole, Mass. under the specification of Webline No. F6211 is comprised of a non-woven, carded rayon which has been bonded with an acrylic latex. This particular material has a caliper of approximately 5 mils as measured under a load of 1200 grams per square inch.

The machine direction of the topsheet 5 is preferably aligned parallel to beads of adhesive 11 and 12 to align the greatest strength of the topsheet parallel to the waistband portions of the diaper, while the machine direction of the moisture-impervious backsheet 6 is normally aligned perpendicular to beads of adhesive 11 and 12 due to manufacturing convenience.

Adhesive beads 11 and 12 may be comprised of any suitable adhesive such as Eastobond No. A-3, a hot melt adhesive available from Eastman Chemical Products, Inc. of Kingsport, Tenn. As pointed out earlier herein, the chief requirement of any adhesive utilized to secure the wet strength tissue envelope directly to the moisture-impervious backsheet is simply that it produce a bond having sufficient strength to cause failure in the wet strength tissue envelope when the backsheet is stripped from the remainder of the diaper. Beads of adhesive 17 and 18 which secure the lowermost layer of wet strength tissue 2 to the overlapping portions of the liquid-pervious topsheet 5 are preferably comprised of the same adhesive employed in beads 11 and 12 so that failure of the wet strength tissue layer 2 normally occurs intermediate adhesive beads 11 and 17 and/or intermediate adhesive beads 12 and 18 when the backsheet is stripped from the diaper. An adhesive having relatively high strength in shear to resist in use delamination and relatively low strength in peel to facilitate stripping of the backsheet is preferably utilized to bond the moisture-impervious backsheet 6 to the liquid-pervious topsheet 5, i.e., beads of adhesive 7, 8, 15 and 16. As pointed out earlier herein, beads of adhesive 9 and 10 securing the liquid-pervious topsheet 5 to the uppermost layer of wet strength tissue 4 are generally comprised of the same adhesive employed in beads 7 and 8. One material found particularly suitable in this service is National Starch No. 34-2933, a hot melt adhesive which is available from the National Starch and Chemical Corporation of Plainfield, N.J.

The present invention has been described in particular detail with reference to several preferred embodiments, and it is not intended to hereby limit to the particular embodiments shown or described. Many other variations of the present invention will be apparent to those skilled in the art.

What is claimed is:

1. In a disposable diaper having a liquid-retaining backsheet, a liquid-absorbent pad comprised of a liquid-absorbent media contained within an envelope of wet strength tissue superimposed on said liquid-retaining backsheet and a liquid-pervious topsheet secured in superposed relation to said liquid-absorbent pad and said liquid-retaining backsheet, the improvement which comprises attachment means for securing at least a portion of said wet strength tissue envelope located adjacent said liquid-retaining backsheet directly to said backsheet, said attachment means and said liquid-retaining backsheet having greater strength than said wet strength tissue envelope, whereby said wet strength tissue envelope is ruptured to provide exposure of the liquid-absorbent media contained therein when said backsheet is stripped from said diaper.

2. The disposable diaper of claim 1, wherein said attachment means for securing said wet strength tissue envelope directly to said liquid-retaining backsheet is comprised of at least one adhesive bead located intermediate said wet strength tissue envelope and said backsheet and extending substantially across the entire width of said liquid-absorbent pad.

3. The disposable diaper of claim 1, wherein said attachment means for securing said wet strength tissue envelope directly to said liquid-retaining backsheet is comprised of a pair of adhesive beads, each adhesive bead being located intermediate said wet strength tissue envelope and said backsheet and positioned near the respective end portions of said diaper, each adhesive bead extending substantially across the entire width of said liquid-absorbent pad.

4. The disposable diaper of claim 1, wherein said attachment means for securing said wet strength tissue envelope to said backsheet is comprised of a layer of adhesive co-extensive with the area of common interface between said wet strength tissue envelope and said backsheet.

5. The disposable diaper of claim 1, wherein said liquid-absorbent media is comprised of airfelt and said wet strength tissue envelope is comprised of tissue paper having a wet tensile strength of at least about 55 grams per inch, as measured in the cross-machine direction.

6. The disposable diaper of claim 1, wherein said wet strength tissue envelope is comprised of a multiplicity of layers of tissue paper, each layer having a wet tensile strength of at least about 55 grams per inch, as measured in the cross-machine direction.

7. The disposable diaper of claim 5, wherein said liquid-pervious topsheet has a wet tensile strength of at least about 1,000 grams per inch as measured in the machine direction and at least about 180 grams per inch as measured in the cross-machine direction.

8. The disposable diaper of claim 7, wherein said liquid-retaining backsheet is comprised of polyethylene having a machine direction tensile strength, as measured at 25 percent elongation, of at least about 800 grams per inch.

* * * * *